US012490967B2

(12) United States Patent
Balkovec

(10) Patent No.: US 12,490,967 B2
(45) Date of Patent: *Dec. 9, 2025

(54) TISSUE-SPREADER ASSEMBLY

(71) Applicant: Boston Scientific Medical Device Limited, Galway (IE)

(72) Inventor: Christian Balkovec, Cambridge (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,925

(22) Filed: Feb. 19, 2024

(65) Prior Publication Data

US 2024/0245393 A1 Jul. 25, 2024

Related U.S. Application Data

(63) Continuation of application No. 17/350,075, filed on Jun. 17, 2021, now Pat. No. 11,937,796.

(60) Provisional application No. 63/040,593, filed on Jun. 18, 2020.

(51) Int. Cl.
*A61B 17/02* (2006.01)

(52) U.S. Cl.
CPC .................................... *A61B 17/02* (2013.01)

(58) Field of Classification Search
CPC ...................................................... A61B 17/02
USPC .................................................. 600/201–245
See application file for complete search history.

(56) References Cited

U.S. PATENT DOCUMENTS

| | | | |
|---|---|---|---|
| 175,254 | A | 3/1876 | Oberly |
| 827,626 | A | 7/1906 | Gillet |
| 848,711 | A | 4/1907 | Daniel |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |

(Continued)

OTHER PUBLICATIONS

Rook Epicardial Access Device Study, ClinicalTrials.gov Identifier: NCT03427333, https://clinicaltrials.gov/ct2/show/NCT03427333, First Posted Online : Feb. 9, 2018.

*Primary Examiner* — Eduardo C Robert
*Assistant Examiner* — Tara Rose E Carter
(74) *Attorney, Agent, or Firm* — Nelson Mullins Riley & Scarborough LLP

(57) ABSTRACT

A tissue-spreader assembly is configured to be selectively inserted into a patient having a first biological tissue and a second biological tissue, and to be maneuvered proximate to the second biological tissue. The tissue-spreader assembly is also configured to selectively engage, at least in part, an area of the second biological tissue without engaging the first biological tissue. The tissue-spreader assembly is also configured to selectively spread, at least in part, the area of the second biological tissue, and maintain the area of the second biological tissue in a spread-apart condition after the tissue-spreader assembly, in use, selectively engages, at least in part, the area of the second biological tissue.

19 Claims, 8 Drawing Sheets

(56) References Cited

U.S. PATENT DOCUMENTS

| | | | |
|---|---|---|---|
| 4,129,129 A | 12/1978 | Amrine | |
| 4,244,362 A | 1/1981 | Anderson | |
| 4,401,124 A | 8/1983 | Guess et al. | |
| 4,639,252 A | 1/1987 | Kelly et al. | |
| 4,641,649 A | 2/1987 | Walinsky et al. | |
| 4,669,467 A | 6/1987 | Willett et al. | |
| 4,682,596 A | 7/1987 | Bales et al. | |
| 4,790,311 A | 12/1988 | Ruiz | |
| 4,790,809 A | 12/1988 | Kuntz | |
| 4,793,350 A | 12/1988 | Mar et al. | |
| 4,807,620 A | 2/1989 | Strul et al. | |
| 4,832,048 A | 5/1989 | Cohen | |
| 4,840,622 A | 6/1989 | Hardy | |
| 4,863,441 A | 9/1989 | Lindsay et al. | |
| 4,884,567 A | 12/1989 | Elliott et al. | |
| 4,892,104 A | 1/1990 | Ito et al. | |
| 4,896,671 A | 1/1990 | Cunningham et al. | |
| 4,928,693 A | 5/1990 | Goodin et al. | |
| 4,936,281 A | 6/1990 | Stasz | |
| 4,960,410 A | 10/1990 | Pinchuk | |
| 4,977,897 A | 12/1990 | Hurwitz | |
| 4,998,933 A | 3/1991 | Eggers et al. | |
| 5,006,119 A | 4/1991 | Acker et al. | |
| 5,019,076 A | 5/1991 | Yamanashi et al. | |
| 5,047,026 A | 9/1991 | Rydell | |
| 5,081,997 A | 1/1992 | Bosley et al. | |
| 5,098,431 A | 3/1992 | Rydell | |
| 5,112,048 A | 5/1992 | Kienle | |
| 5,154,724 A | 10/1992 | Andrews | |
| 5,201,756 A | 4/1993 | Horzewski et al. | |
| 5,209,741 A | 5/1993 | Spaeth | |
| 5,211,183 A | 5/1993 | Wilson | |
| 5,221,256 A | 6/1993 | Mahurkar | |
| 5,230,349 A | 7/1993 | Langberg | |
| 5,279,575 A * | 1/1994 | Sugarbaker | A61B 17/3403 606/1 |
| 5,281,216 A | 1/1994 | Klicek | |
| 5,300,068 A | 4/1994 | Rosar et al. | |
| 5,300,069 A | 4/1994 | Hunsberger et al. | |
| 5,314,418 A | 5/1994 | Takano et al. | |
| 5,318,525 A | 6/1994 | West et al. | |
| 5,327,905 A | 7/1994 | Avitall | |
| 5,364,393 A | 11/1994 | Auth et al. | |
| 5,372,596 A | 12/1994 | Klicek et al. | |
| 5,380,304 A | 1/1995 | Parker | |
| 5,397,304 A | 3/1995 | Truckai | |
| 5,403,338 A | 4/1995 | Milo | |
| 5,423,809 A | 6/1995 | Klicek | |
| 5,425,382 A | 6/1995 | Golden et al. | |
| 5,490,859 A | 2/1996 | Mische et al. | |
| 5,497,774 A | 3/1996 | Swartz et al. | |
| 5,507,751 A | 4/1996 | Goode et al. | |
| 5,509,411 A | 4/1996 | Littmann et al. | |
| 5,540,681 A | 7/1996 | Strul et al. | |
| 5,545,200 A | 8/1996 | West et al. | |
| 5,555,618 A | 9/1996 | Winkler | |
| 5,571,088 A | 11/1996 | Lennox et al. | |
| 5,575,766 A | 11/1996 | Swartz et al. | |
| 5,575,772 A | 11/1996 | Lennox | |
| 5,599,347 A | 2/1997 | Hart et al. | |
| 5,605,162 A | 2/1997 | Mirzaee et al. | |
| 5,617,878 A | 4/1997 | Taheri | |
| 5,622,169 A | 4/1997 | Golden et al. | |
| 5,624,430 A | 4/1997 | Eton et al. | |
| 5,667,488 A | 9/1997 | Lundquist et al. | |
| 5,673,695 A | 10/1997 | McGee et al. | |
| 5,674,208 A | 10/1997 | Berg et al. | |
| 5,683,366 A | 11/1997 | Eggers et al. | |
| 5,720,744 A | 2/1998 | Eggleston et al. | |
| 5,741,249 A | 4/1998 | Moss et al. | |
| 5,766,135 A | 6/1998 | Terwilliger | |
| 5,779,688 A | 7/1998 | Imran et al. | |
| 5,810,764 A | 9/1998 | Eggers et al. | |
| 5,814,028 A | 9/1998 | Swartz et al. | |
| 5,830,214 A | 11/1998 | Flom et al. | |
| 5,836,875 A | 11/1998 | Webster, Jr. | |
| 5,849,011 A | 12/1998 | Jones et al. | |
| 5,851,210 A | 12/1998 | Torossian | |
| 5,885,227 A | 3/1999 | Finlayson | |
| 5,888,201 A | 3/1999 | Stinson et al. | |
| 5,893,848 A | 4/1999 | Negus et al. | |
| 5,893,885 A | 4/1999 | Webster, Jr. | |
| 5,904,679 A | 5/1999 | Clayman | |
| 5,916,210 A | 6/1999 | Winston | |
| 5,921,957 A | 7/1999 | Killion et al. | |
| 5,931,818 A | 8/1999 | Werp et al. | |
| 5,944,023 A | 8/1999 | Johnson et al. | |
| 5,951,482 A | 9/1999 | Winston et al. | |
| 5,957,842 A | 9/1999 | Littmann et al. | |
| 5,964,757 A | 10/1999 | Ponzi | |
| 5,967,976 A | 10/1999 | Larsen et al. | |
| 5,989,276 A | 11/1999 | Houser et al. | |
| 6,007,555 A | 12/1999 | Devine | |
| 6,009,877 A | 1/2000 | Edwards | |
| 6,013,072 A | 1/2000 | Winston et al. | |
| 6,017,340 A | 1/2000 | Cassidy et al. | |
| 6,018,676 A | 1/2000 | Davis et al. | |
| 6,030,380 A | 2/2000 | Auth et al. | |
| 6,032,674 A | 3/2000 | Eggers et al. | |
| 6,048,349 A | 4/2000 | Winston et al. | |
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Laufer et al. | |
| 6,117,131 A | 9/2000 | Taylor | |
| 6,142,992 A | 11/2000 | Cheng et al. | |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | DeVore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |
| 6,360,128 B2 | 3/2002 | Kordis et al. | |
| 6,364,877 B1 | 4/2002 | Goble et al. | |
| 6,385,472 B1 | 5/2002 | Hall et al. | |
| 6,394,976 B1 | 5/2002 | Winston et al. | |
| 6,395,002 B1 | 5/2002 | Ellman et al. | |
| 6,419,674 B1 | 7/2002 | Bowser et al. | |
| 6,428,551 B1 | 8/2002 | Hall et al. | |
| 6,450,989 B2 | 9/2002 | Dubrul et al. | |
| 6,475,214 B1 | 11/2002 | Moaddeb | |
| 6,485,485 B1 | 11/2002 | Winston et al. | |
| 6,508,754 B1 | 1/2003 | Liprie et al. | |
| 6,524,303 B1 | 2/2003 | Garibaldi | |
| 6,530,923 B1 | 3/2003 | Dubrul et al. | |
| 6,554,827 B2 | 4/2003 | Chandrasekaran et al. | |
| 6,562,031 B2 | 5/2003 | Chandrasekaran et al. | |
| 6,562,049 B1 | 5/2003 | Norlander et al. | |
| 6,565,562 B1 | 5/2003 | Shah et al. | |
| 6,607,529 B1 | 8/2003 | Jones et al. | |
| 6,632,222 B1 | 10/2003 | Edwards et al. | |
| 6,639,999 B1 | 10/2003 | Cookingham et al. | |
| 6,650,923 B1 | 11/2003 | Lesh et al. | |
| 6,651,672 B2 | 11/2003 | Roth | |
| 6,662,034 B2 | 12/2003 | Segner et al. | |

(56) References Cited

U.S. PATENT DOCUMENTS 6,663,621 B1 12/2003 Winston et al.
6,702,811 B2 3/2004 Stewart et al.
6,709,444 B1 3/2004 Makower
6,723,052 B2 4/2004 Mills
6,733,511 B2 5/2004 Hall et al.
6,740,103 B2 5/2004 Hall et al.
6,752,800 B1 6/2004 Winston et al.
6,755,816 B2 6/2004 Ritter et al.
6,811,544 B2 11/2004 Schaer
6,814,733 B2 11/2004 Schwartz et al.
6,820,614 B2 11/2004 Bonutti
6,834,201 B2 12/2004 Gillies et al.
6,842,639 B1 1/2005 Winston et al.
6,852,109 B2 2/2005 Winston et al.
6,855,143 B2 2/2005 Davison et al.
6,860,856 B2 3/2005 Ward et al.
6,869,431 B2 3/2005 Maguire et al.
6,911,026 B1 6/2005 Hall et al.
6,951,554 B2 10/2005 Johansen et al.
6,951,555 B1 10/2005 Suresh et al.
6,955,675 B2 10/2005 Jain
6,970,732 B2 11/2005 Winston et al.
6,980,843 B2 12/2005 Eng et al.
7,029,470 B2 4/2006 Francischelli et al.
7,056,294 B2 6/2006 Khairkhahan et al.
7,083,566 B2 8/2006 Tornes et al.
7,112,197 B2 9/2006 Hartley et al.
7,335,197 B2 2/2008 Sage et al.
7,618,430 B2 11/2009 Scheib
7,651,492 B2 1/2010 Wham
7,666,203 B2 2/2010 Chanduszko et al.
7,678,081 B2 3/2010 Whiting et al.
7,682,360 B2 3/2010 Guerra
7,828,796 B2 11/2010 Wong et al.
7,900,928 B2 3/2011 Held et al.
8,192,425 B2 6/2012 Mirza et al.
8,257,323 B2 9/2012 Joseph et al.
8,388,549 B2 3/2013 Paul et al.
8,500,697 B2 8/2013 Kurth et al.
11,339,579 B1 5/2022 Stearns
11,937,796 B2 * 3/2024 Balkovec ............. A61B 18/148
2001/0012934 A1 8/2001 Chandrasekaran et al.
2001/0021867 A1 9/2001 Kordis et al.
2002/0019644 A1 2/2002 Hastings et al.
2002/0022781 A1 2/2002 Mclntire et al.
2002/0022836 A1 2/2002 Goble et al.
2002/0035361 A1 3/2002 Houser et al.
2002/0087153 A1 7/2002 Roschak et al.
2002/0087156 A1 7/2002 Maguire et al.
2002/0111618 A1 8/2002 Stewart et al.
2002/0123749 A1 9/2002 Jain
2002/0147485 A1 10/2002 Mamo et al.
2002/0169377 A1 11/2002 Khairkhahan et al.
2002/0188302 A1 12/2002 Berg et al.
2002/0198521 A1 12/2002 Maguire
2003/0032929 A1 2/2003 McGuckin
2003/0040742 A1 2/2003 Underwood et al.
2003/0144658 A1 7/2003 Schwartz et al.
2003/0158480 A1 8/2003 Tornes et al.
2003/0163153 A1 8/2003 Scheib
2003/0225392 A1 12/2003 McMichael et al.
2004/0015162 A1 1/2004 McGaffigan
2004/0024396 A1 2/2004 Eggers
2004/0030328 A1 2/2004 Eggers et al.
2004/0044350 A1 3/2004 Martin et al.
2004/0073243 A1 4/2004 Sepetka et al.
2004/0077948 A1 4/2004 Violante et al.
2004/0116851 A1 6/2004 Johansen et al.
2004/0127963 A1 7/2004 Uchida et al.
2004/0133113 A1 7/2004 Krishnan
2004/0133130 A1 7/2004 Ferry et al.
2004/0143256 A1 7/2004 Bednarek
2004/0147950 A1 7/2004 Mueller et al.
2004/0181213 A1 9/2004 Gondo
2004/0230188 A1 11/2004 Cioanta et al.
2005/0004585 A1 1/2005 Hall et al.
2005/0010208 A1 1/2005 Winston et al.
2005/0049628 A1 3/2005 Schweikert et al.
2005/0059966 A1 3/2005 McClurken et al.
2005/0065507 A1 3/2005 Hartley et al.
2005/0085806 A1 4/2005 Auge et al.
2005/0096529 A1 5/2005 Cooper et al.
2005/0101984 A1 5/2005 Chanduszko et al.
2005/0119556 A1 6/2005 Gillies et al.
2005/0137527 A1 6/2005 Kunin
2005/0149012 A1 7/2005 Penny et al.
2005/0203504 A1 9/2005 Wham et al.
2005/0203507 A1 9/2005 Truckai et al.
2005/0261607 A1 11/2005 Johansen et al.
2005/0288631 A1 12/2005 Lewis et al.
2006/0041253 A1 2/2006 Newton et al.
2006/0074398 A1 4/2006 Whiting et al.
2006/0079769 A1 4/2006 Whiting et al.
2006/0079787 A1 4/2006 Whiting et al.
2006/0079884 A1 4/2006 Manzo et al.
2006/0085054 A1 4/2006 Zikorus et al.
2006/0089638 A1 4/2006 Carmel et al.
2006/0106375 A1 5/2006 Werneth et al.
2006/0135962 A1 6/2006 Kick et al.
2006/0142756 A1 6/2006 Davies et al.
2006/0189972 A1 8/2006 Grossman
2006/0241586 A1 10/2006 Wilk
2006/0247672 A1 11/2006 Vidlund et al.
2006/0264927 A1 11/2006 Ryan
2006/0276710 A1 12/2006 Krishnan
2007/0060879 A1 3/2007 Weitzner et al.
2007/0066975 A1 3/2007 Wong et al.
2007/0118099 A1 5/2007 Trout, III
2007/0123964 A1 5/2007 Davies et al.
2007/0167775 A1 7/2007 Kochavi et al.
2007/0208256 A1 9/2007 Marilla
2007/0213595 A1 * 9/2007 Ravikumar ........ A61B 17/0218
600/217
2007/0225681 A1 9/2007 House
2007/0270791 A1 11/2007 Wang et al.
2008/0039865 A1 2/2008 Shaher et al.
2008/0042360 A1 2/2008 Veikley
2008/0086120 A1 4/2008 Mirza et al.
2008/0097213 A1 4/2008 Carlson et al.
2008/0108987 A1 5/2008 Bruszewski et al.
2008/0146918 A1 6/2008 Magnin et al.
2008/0171934 A1 7/2008 Greenan et al.
2008/0208121 A1 8/2008 Youssef et al.
2008/0275439 A1 11/2008 Francischelli et al.
2009/0105742 A1 4/2009 Kurth et al.
2009/0138009 A1 5/2009 Viswanathan et al.
2009/0163850 A1 6/2009 Betts et al.
2009/0177114 A1 7/2009 Chin et al.
2009/0264977 A1 10/2009 Bruszewski et al.
2010/0087789 A1 4/2010 Leeflang et al.
2010/0125282 A1 5/2010 Machek et al.
2010/0168684 A1 7/2010 Ryan
2010/0179632 A1 7/2010 Bruszewski et al.
2010/0191142 A1 7/2010 Paul et al.
2010/0194047 A1 8/2010 Sauerwine
2011/0046619 A1 2/2011 Ducharme
2011/0152716 A1 6/2011 Chudzik et al.
2011/0160592 A1 6/2011 Mitchell
2011/0190763 A1 8/2011 Urban et al.
2012/0232546 A1 9/2012 Mirza et al.
2012/0265055 A1 10/2012 Melsheimer et al.
2012/0330156 A1 12/2012 Brown et al.
2013/0184551 A1 7/2013 Paganelli et al.
2013/0184735 A1 7/2013 Fischell et al.
2013/0282084 A1 10/2013 Mathur et al.
2014/0206987 A1 7/2014 Urbanski et al.
2014/0296769 A1 10/2014 Hyde et al.
2016/0206338 A1 7/2016 Allen et al.
2016/0220741 A1 8/2016 Garrison et al.
2019/0021763 A1 1/2019 Zhou et al.
2019/0247035 A1 8/2019 Gittard et al.

* cited by examiner

TISSUE-SPREADER ASSEMBLY

CROSS REFERENCE TO RELATED APPLICATIONS

The present application is a continuation of and claims benefit of U.S. patent application Ser. No. 17/350,075, entitled “TISSUE-SPREADER ASSEMBLY,” filed Jun. 17, 2021, which claims the benefit of U.S. Provisional Patent Application 63/040,593, entitled “TISSUE-SPREADER ASSEMBLY,” filed Jun. 18, 2020, all of which are hereby incorporated in their entirety.

TECHNICAL FIELD

This document relates to the technical field of (and is not limited to) a tissue-spreader assembly (and method therefor).

BACKGROUND

Known medical devices are configured to facilitate a medical procedure and help healthcare providers diagnose and/or treat medical conditions of sick patients.

SUMMARY

It will be appreciated that there exists a need to mitigate (at least in part) at least one problem associated with the existing (known) tissue spreaders (also called the existing technology). After much study of, and experimentation with, the existing (known) tissue spreaders, an understanding (at least in part) of the problem and its solution have been identified (at least in part) and are articulated (at least in part) as follows:

Gaining epicardial access involves piercing the thin pericardial layer that surrounds the heart (of the patient) without puncturing the myocardium (the heart muscle that is encapsulated by the pericardial layer). This might be likened to trying to puncture a thin layer of plastic wrap surrounding (wrapped around) a steak without puncturing (or damaging) the steak itself.

Known mechanical needles are configured to puncture the pericardium layer, where the user might be required to precisely control the amount of input force and/or displacement to be applied to the pericardium layer (via the needle, etc.) in order to avoid inadvertently puncturing (damaging) the myocardium.

Sometimes, the amount of force input required to puncture the pericardium layer might be the same as, or similar to, the amount of force input required to puncture the myocardium. Given that the pericardium layer and the myocardium layer are in such close proximity to one another, it might be unavoidable to puncture the myocardium layer (while puncturing the pericardium layer) when trying to gain epicardial access (in the heart of the patient).

For instance, there are known devices configured to pull the pericardium layer back from the myocardium layer in order to facilitate easier and safer puncturing of the pericardium layer. In doing this, the known devices might stretch a region of the pericardium layer, increasing the stress in the tissue and making the pericardium layer easier to puncture. These known devices embed themselves in the pericardial layer (tissue) in order to gain a foothold and allow a user to separate the two tissues (the pericardium layer and the myocardium layer). Along these same lines, if a device gains a foothold (or differentially grip) the pericardium layer from the myocardium layer, and uses the grip to spread out the pericardium layer over top of the myocardium layer, it might increase the stress in the pericardium layer relative to the myocardium layer, and facilitate easier (less risky) puncturing of the pericardium layer without inadvertently imparting damage to the myocardium layer.

To mitigate, at least in part, at least one problem associated with the existing technology, there is provided (in accordance with a major aspect) an apparatus. The apparatus includes and is not limited to (comprises) a tissue-spreader assembly. The tissue-spreader assembly is configured to be selectively inserted into a patient having a first biological tissue and a second biological tissue positioned proximate to the first biological tissue. The tissue-spreader assembly is also configured to be maneuvered proximate to the second biological tissue. The tissue-spreader assembly is also configured to selectively engage, at least in part, an area of the second biological tissue without engaging the first biological tissue after the tissue-spreader assembly, in use, is maneuvered proximate to the second biological tissue. The tissue-spreader assembly is also configured to selectively spread, at least in part, the area of the second biological tissue, and maintain the area of the second biological tissue in a spread-apart condition (this is done, preferably, after the tissue-spreader assembly, in use, selectively engages, at least in part, the area of the second biological tissue without engaging the first biological tissue).

To mitigate, at least in part, at least one problem associated with the existing technology, there is provided (in accordance with a major aspect) a method. The method is for selectively spreading a second biological tissue positioned proximate to a first biological tissue of a patient. The method includes and is not limited to (comprises) selectively inserting a tissue-spreader assembly into the patient. The method also includes maneuvering the tissue-spreader assembly to a position located proximate to the second biological tissue. The method also includes using the tissue-spreader assembly to selectively engage, at least in part, an area of the second biological tissue without engaging the first biological tissue after the tissue-spreader assembly, in use, is maneuvered proximate to the second biological tissue. The method also includes using the tissue-spreader assembly to selectively spread, at least in part, the area of the second biological tissue, and maintain the area of the second biological tissue in a spread-apart condition (this is done, preferably, after the tissue-spreader assembly, in use, selectively engages, at least in part, the area of the second biological tissue without engaging the first biological tissue).

Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
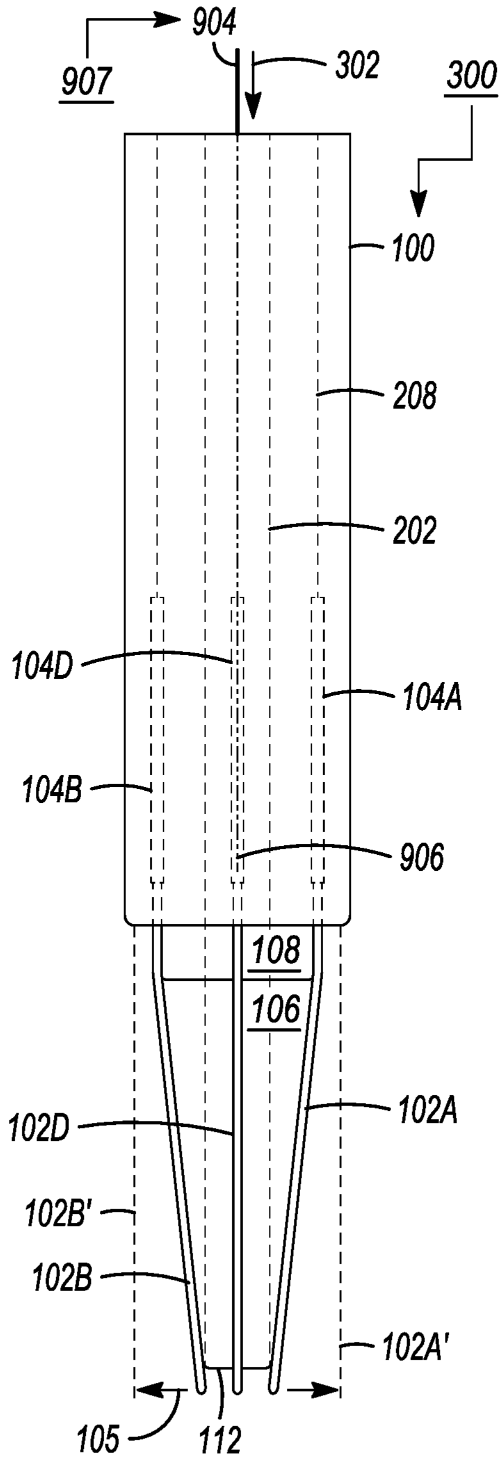
FIG. 1, FIG. 2 and FIG. 3 depict side perspective views (FIG. 1 and FIG. 2) and a cross-sectional view (FIG. 3) of embodiments of a tissue-spreader assembly.

The drawings are not necessarily to scale and may be illustrated by phantom lines, diagrammatic representations, and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary, or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 2:
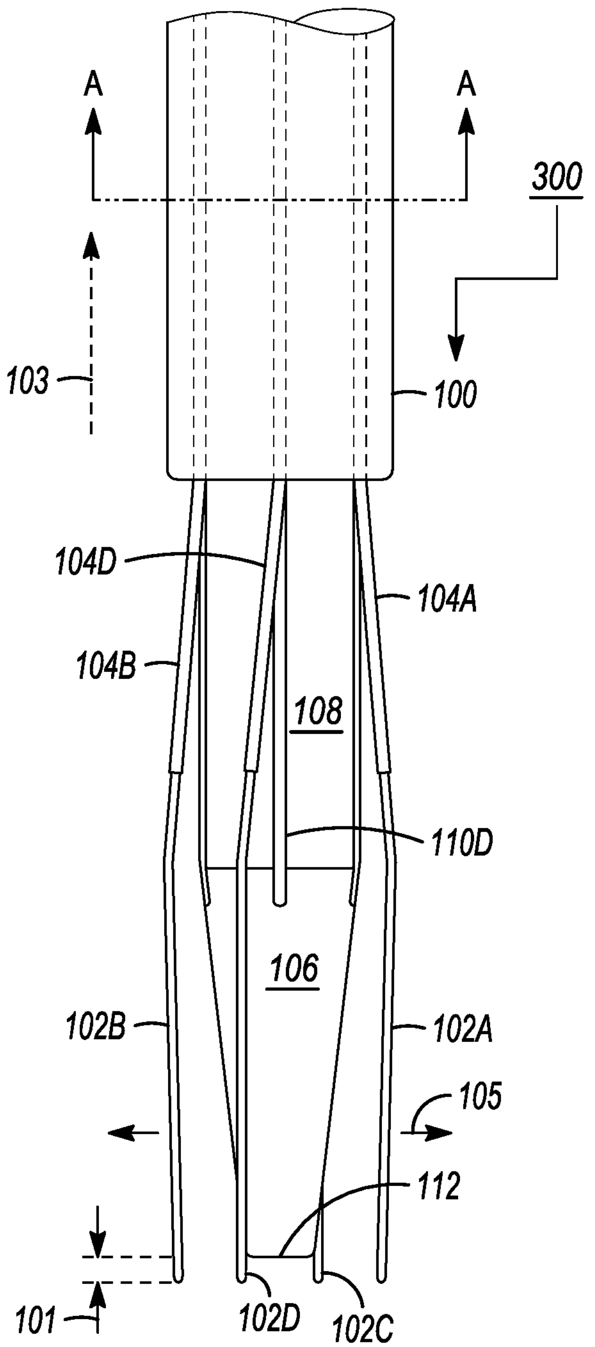
Figure 3:
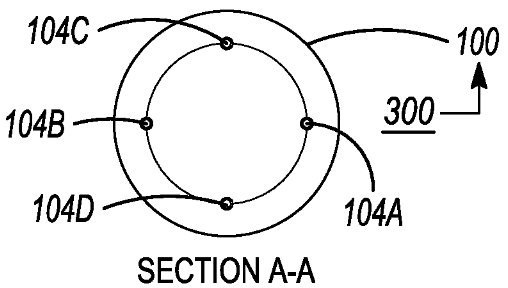

FIG. 1, FIG. 2 and FIG. 3 depict side perspective views (FIG. 1 and FIG. 2) and a cross-sectional view (FIG. 3) of embodiments of a tissue-spreader assembly 300.

Referring to the embodiment as depicted in FIG. 1, the tissue-spreader assembly 300 is depicted in an undeployed condition. The undeployed condition may be called a non-spread condition, a contained position, a storage condition, etc., and any equivalent thereof. The tissue-spreader assembly 300 is configured to be inserted into a confined space defined by a living body (the patient), etc.

Referring to the embodiment as depicted in FIG. 2, the tissue-spreader assembly 300 is depicted in the deployed condition (also called the spread configuration, etc., and any equivalent thereof). The tissue-spreader assembly 300 includes, preferably, components having biocompatible material properties suitable for sufficient and/or safe performance (such as dielectric strength, thermal, insulation, corrosion, water and/or heat resistance, etc.), for compliance with industrial and regulatory safety standards (or compatible for medical usage), etc. Reference may be made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 1, the tissue-spreader assembly 300 includes a first tube 100 (also called an outer tube) and a second tube 108 (also called an inner tube). The first tube 100 and the second tube 108 are configured to interact (cooperate) with each other. The second tube 108 is configured to be received within (and along) a longitudinal length of the first tube 100. The first tube 100 and the second tube 108 are configured to be coaxially aligned (and movably slidable) with each other once the second tube 108 is received within, and along, the longitudinal length of the first tube 100. Preferably, the second tube 108 is slidably receivable (movable) along the longitudinal axis extending along the first tube lumen 208 of the first tube 100 by application of a movement force, etc., by the user, either directly or indirectly. The first tube 100 may be called a containing sheath, and any equivalent thereof. The first tube 100 defines the first tube lumen 208 configured to slidably receive the second tube 108 (therein and therealong). The second tube 108 is configured to be received within the first tube lumen 208 of the first tube 100. The second tube 108 has, preferably, a sufficiently rigid property (and/or is substantially not flexible) within an acceptable degree of tolerance, so that the second tube 108 may be pushed through tissue (if so required). The second tube 108 defines the second tube lumen 202 (extending along a longitudinal length of the second tube 108). The distal tip section 106 extends (depends) from an end portion (distal portion) of the second tube 108. The distal tip section 106 also defines (at least in part) the second tube lumen 202. The distal tip section 106 forms (provides), preferably, an elongated cone section (a frustoconical shape, a cone formation) that extends from the distal portion of the second tube 108 (to improve the ability of insertion of the second tube 108 into tissue, if so required).

Referring to the embodiment as depicted in FIG. 1, the biased bowed portions (104A, 104B, 104C, 104D) are positioned between the first tube 100 and the second tube 108 once (after) the tissue-spreader assembly 300 is placed in the undeployed condition, as depicted in FIG. 1. In the undeployed condition, the first tube 100 is configured to substantially cover the second tube 108 so that the biased bowed portions (104A, 104B, 104C, 104D) may remain covered by the first tube 100. The first tube 100 is positioned over top of (configured to selectively cover) the biased bowed portions (104A, 104B, 104C, 104D) in the undeployed condition (as depicted in FIG. 1). The biased bowed portions (104A, 104B, 104C, 104D) face (contact, are positioned proximate to) the inner surface (of the first tube 100) forming the first tube lumen 208 (of the first tube 100) in the undeployed condition. The biased bowed portions (104A, 104B, 104C, 104D) face (contact, are positioned proximate to) the outer surface of the second tube 108 in the undeployed condition. The biased bowed portions (104A, 104B, 104C, 104D) may include bowed metal pieces, spring-biased components, biased portions, etc., and any equivalent thereof. This arrangement (as depicted in FIG. 1) compresses the biased bowed portions (104A, 104B, 104C, 104D), and forces the biased bowed portions (104A, 104B, 104C, 104D) to run parallel (to become aligned in a parallel relationship) to the second tube 108 in the undeployed condition (as depicted in FIG. 1).

Referring to the embodiment as depicted in FIG. 1, the biased bowed portions (104A, 104B, 104C, 104D) are configured to be positioned between the first tube 100 and the second tube 108 after the tissue-spreader assembly 300 is placed in an undeployed condition. The biased bowed portions (104A, 104B, 104C, 104D) are also configured to be compressed after the tissue-spreader assembly 300 is placed in an undeployed condition (as depicted in FIG. 1). Once the first tube 100 is moved relative to the second tube 108, the biased bowed portions (104A, 104B, 104C, 104D) are released and may become decompressed, after the tissue-spreader assembly 300 is placed in a deployed condition (as depicted in FIG. 2).

Figure 4:
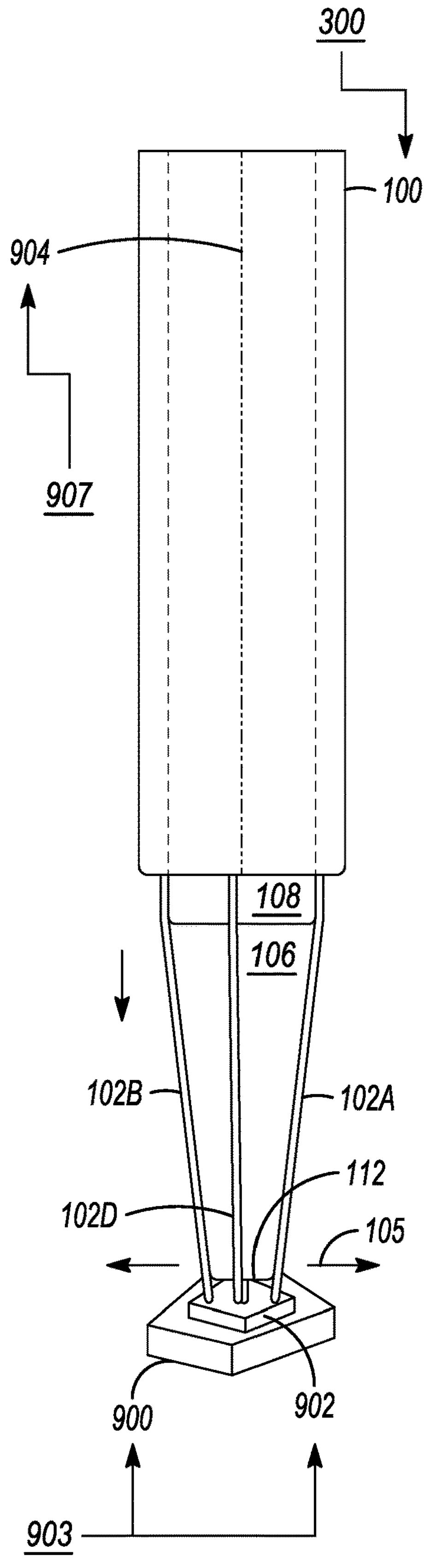
FIG. 4 and FIG. 5 depict side perspective views of embodiments of the tissue-spreader assembly of FIG. 1.
Figure 5:
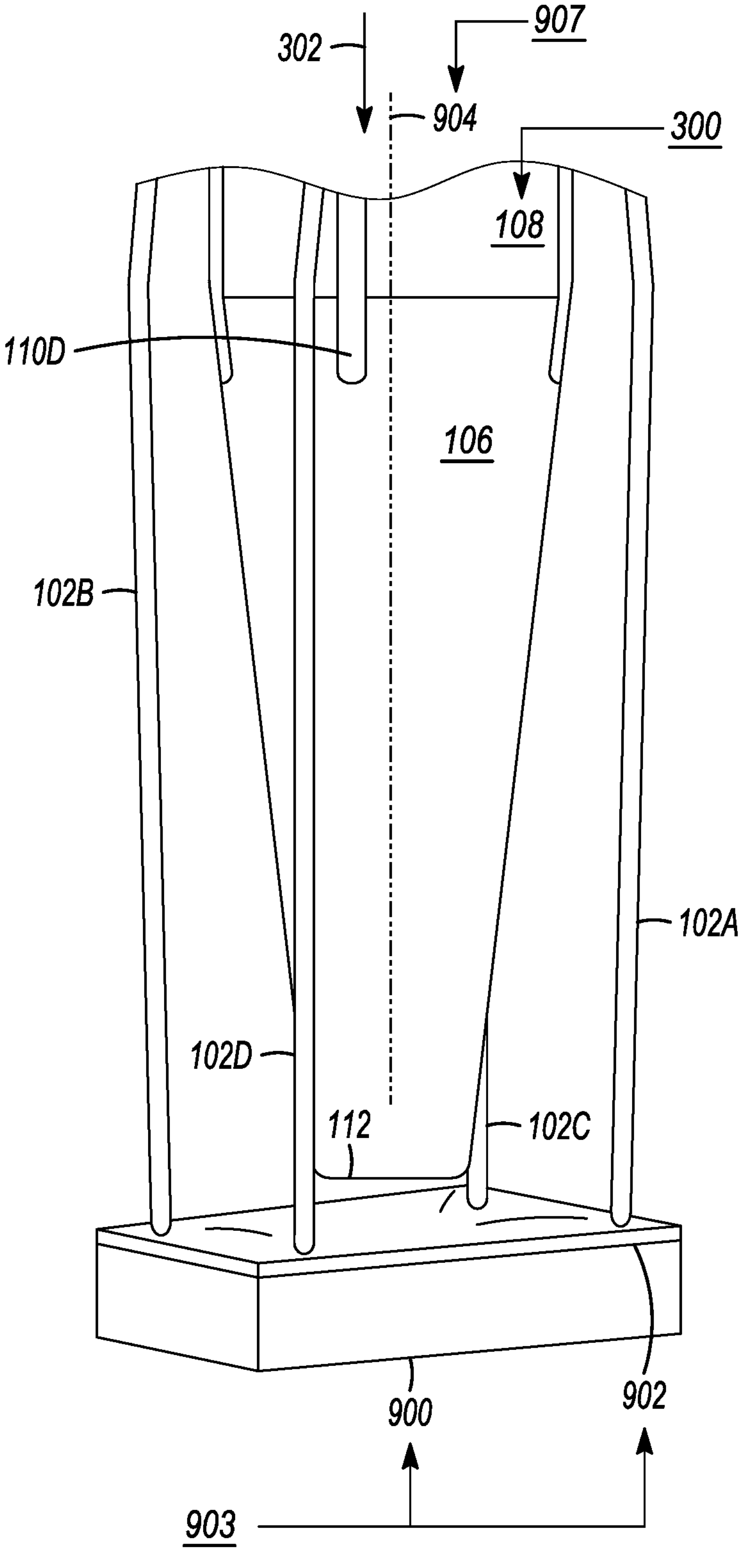

Referring to the embodiment as depicted in FIG. 1, the prongs (102A, 102B, 102C, 102D) are movable between the undeployed condition (as depicted in FIG. 1) and the deployed condition (as depicted in FIG. 2). The prongs (102A, 102B, 102C, 102D) are positioned in the undeployed condition, as depicted in FIG. 1. The prongs (102A, 102B, 102C, 102D) extend, respectively, from the biased bowed portions (104A, 104B, 104C, 104D). The prongs (102A, 102B, 102C, 102D) are configured to engage, at least in part, the area of the second biological tissue 902 (as depicted in FIG. 4 and FIG. 5, etc.). The prongs (102A, 102B, 102C, 102D) may include a metal alloy, etc., and any equivalent thereof. The prongs (102A, 102B, 102C, 102D) may include grippers, thin metal grippers, etc., and any equivalent thereof.

Preferably, the prongs (102A, 102B, 102C, 102D) include hollow tubes with open portals configured to face axially away from the biased bowed portions (104A, 104B, 104C, 104D). The open portals are also configured to be embedded (engaged), at least in part, into the second biological tissue 902 (as depicted in FIG. 4 and/or FIG. 5). The prongs (102A, 102B, 102C, 102D) include, preferably, hollow tubes with open portals configured to face the second biological tissue 902 (as depicted in FIG. 4 and/or FIG. 5) once the tissue-spreader assembly 300 is positioned proximate to the second biological tissue 902. It will be appreciated that the dashed lined prongs (102A', 102B') demonstrate the positions of the prongs (102A, 102B), of FIG. 1, in their respective deployed conditions, while FIG. 2 depicts the prongs (102A, 102B) positioned in their respective deployed conditions, etc. The prongs (102A, 102B) are configured to be movable (laterally movable away from the longitudinal axis extending through the first tube 100) along the prong-movement direction 105 (between their respective deployed conditions, as depicted in FIG. 2, and their respective undeployed conditions as depicted in FIG. 1). The prongs (102A, 102B, 102C, 102D) extend past the distal end of the second tube 108 (as depicted in FIG. 1 and in FIG. 2) whether they are deployed as depicted in FIG. 1 or FIG. 2. The prongs (102A, 102B, 102C, 102D) extend past a distal end of the second tube 108 once (after) the prongs (102A, 102B, 102C, 102D) are moved from the undeployed condition to the deployed condition. The prongs (102A, 102B, 102C, 102D) extend past the tube portal 112 of the second tube 108 (reference is made to FIG. 14 and FIG. 15). The prongs (102A, 102B, 102C, 102D) are configured to be embedded, at least in part, in the second biological tissue 902, and the second biological tissue 902 is positioned over the first biological tissue 900 (for instance, as depicted in FIG. 4 and FIG. 5).

Referring to the embodiment as depicted in FIG. 1, the prongs (102A, 102B, 102C, 102D) and/or the biased bowed portions (104A, 104B, 104C, 104D) may include a shape-memory material configured to be manipulated and/or deformed followed by a return to the original shape that the shape-memory material had been set in (prior to manipulation). Shape-memory materials (SMMs) are known and not further described in detail. Shape-memory materials are configured to recover their original shape from a significant and seemingly plastic deformation in response to a particular stimulus being applied to the shape-memory material. This is known as the shape memory effect (SME). Superelasticity (in alloys) may be observed once the shape-memory material is deformed under the presence (an application) of a stimulus force.

Referring to the embodiment as depicted in FIG. 1, the prongs (102A, 102B, 102C, 102D) and/or the biased bowed portions (104A, 104B, 104C, 104D) may include SAE (Society of Automotive Engineering) Type 304 Stainless Steel. SAE Type 304 stainless steel contains both chromium (from between about 15% to about 20%) and nickel (from between about 2% to about 10.5%) metals as the main non-iron constituents.

Referring to the embodiment as depicted in FIG. 1, an ancillary device 907 is configured to be received (at least in part) along the second tube lumen 202 of the second tube 108. The ancillary device 907 may include, for instance, a puncture device 904 configured to form a puncture through (or simply cut) biological tissue, etc. This is done, preferably, after the puncture device 904 is received along the second tube lumen 202 of the second tube 108 and is positioned accordingly. The puncture device 904 is configured to be movable along the guide path 302 (extending along a length of the second tube lumen 202 extending along, at least in part, a length of the tissue-spreader assembly 300). The puncture device 904 includes, preferably, a distal puncture tip 906 (reference is made to FIG. 9, FIG. 10 and FIG. 11). The ancillary device 907 (or the puncture device 904) is configured to be (at least in part) inserted into, and movable along, the second tube lumen 202. The second tube lumen 202 is, preferably, reinforced for (or provides) sufficient stiffness during insertion of the second tube lumen 202 into the patient (if required). The distal tip section 106 (also called the tapered distal section) is configured, preferably, for ease of insertion of the leading edge of the tissue-spreader assembly 300 through tissue, etc., if required. The prongs (102A, 102B, 102C, 102D) are configured to (positioned to) surround a circumference surface of the distal tip section 106, and extend slightly past the distal tip section 106. The first tube 100 (also called a surrounding sheath) is configured to selectively contain (cover) the prongs (102A, 102B, 102C, 102D), as depicted in FIG. 1. The first tube 100 is configured to be shifted (moved or slid) relative to the second tube 108 to facilitate releasement (biased movement, biased bowing outwards) of the prongs (102A, 102B, 102C, 102D), as depicted in FIG. 2. The ancillary device 907 and/or the puncture device 904 is/are configured to be inserted (at least in part) into the second tube lumen 202 of the second tube 108. The puncture device 904 may include sufficient rigidity for traversing through patient anatomy to gain access (such as to the heart, etc.), if so required. The puncture device 904 is configured, preferably, to prevent creation of a tissue core when traversing the patient anatomy and/or to provide a leading edge configured to facilitate easier traversal through tissue, etc., if so required. The puncture device 904 may include a stylet, a radio-frequency puncture device, etc., and any equivalent thereof. The radio-frequency puncture device may for instance, include (and is not limited to) a radio frequency puncture device, such as the BAYLIS (TRADEMARK) POWERWIRE (REGISTERED TRADEMARK), a radio frequency guidewire manufactured by BAYLIS MEDICAL COMPANY (headquartered in Canada). The radio-frequency puncture device does not, preferably, require mechanical force to puncture tissue, but rather, may rely on the application (emission) of radio frequency energy to the tissue, which vaporizes the tissue and creates (forms) a puncture, etc., through the tissue. The radio-frequency puncture device, with precise applied timing of radio frequency energy, may be used to selectively puncture only the second biological tissue 902 but not the first biological tissue 900 (that is, while not harming or damaging the first biological tissue 900). This condition may be performed via the manipulation or use of: (A) precise pre-tenting force applied with a blunt radio-frequency puncture device (with only enough force applied to the puncture device prior to application of radio frequency energy to facilitate puncture of the second biological tissue 902 when the radio frequency energy is applied); (B) impedance readings to determine when the second biological tissue 902 has been punctured and thus application of the radio frequency energy may be stopped; and/or (C) precise timed application of the radio frequency energy (that is, the radio frequency energy may only be turned on for a period of time where the second biological tissue 902 is punctured without puncturing and/or damaging the first biological tissue 900). Impedance measurements or impedance readings (from the tissue) may indicate when the space has been formed through the second biological tissue 902 and may indicate to a user when to stop applying force to the puncture device, etc., to avoid damaging the first biological tissue 900. Ultrasound readings, from an ultrasound emitter (known and not depicted), may allow a user to determine when they have punctured the second biological tissue 902 and may indicate that the user may stop applying puncture force, etc., to avoid damaging the first biological tissue 900. A laser measuring device (known and not depicted) may be used for measuring tissue properties and determining when the space has been formed through the second biological tissue 902 (this arrangement might be used to indicate when the chosen puncture modality might cease operation).

Referring to the embodiment as depicted in FIG. 1, the first tube 100 is configured to force (move) the biased bowed portions (104A, 104B, 104C, 104D) to be pressed against the body of the second tube 108, once the first tube 100 is moved coaxially along the second tube 108. The first tube 100 is configured to compress the biased bowed portions (104A, 104B, 104C, 104D) in response to the first tube 100 being moved to cover the biased bowed portions (104A, 104B, 104C, 104D), as depicted in FIG. 1. The longitudinal length of the first tube 100 is, preferably, sufficient to cover the biased bowed portions (104A, 104B, 104C, 104D) on (at) a distal portion of the second tube 108. The first tube 100 is configured to be manipulated (moved), proximally, to selectively move (coaxially) along the second tube 108 (by the user via linkages, etc., known and not depicted). The tissue-spreader assembly 300 (or the first tube 100) is configured to operate and (in concert with the other components) facilitate the stretching of the second biological tissue 902. The first tube 100 has an inner diameter that is compatible with the outer diameter of second tube 108 and the biased bowed portions (104A, 104B, 104C, 104D) for cooperative action. The first tube 100 is configured to reduce the bow angle formed by the biased bowed portions (104A, 104B, 104C, 104D), as depicted in FIG. 2, to about, preferably, zero (0) degrees as depicted in FIG. 1; that is, the biased bowed portions (104A, 104B, 104C, 104D) become aligned substantially parallel (in a parallel relationship) with a longitudinal length of the second tube 108. The first tube 100 is configured to maneuver the prongs (102A, 102B, 102C, 102D), which extend from the biased bowed portions (104A, 104B, 104C, 104D), from the undeployed condition (as depicted in FIG. 1) to the deployed condition (as depicted in FIG. 2); this is done (preferably) once (or after) the first tube 100 is moved (retracted) away from the tube portal 112 (or the distal tip section 106) (as depicted in FIG. 2); that is once (or after) the first tube 100 is retracted proximally over (and along) the second tube 108 (as depicted in FIG. 2).

Referring to the embodiment as depicted in FIG. 1, the prongs (102A, 102B, 102C, 102D) extend from the biased bowed portions (104A, 104B, 104C, 104D). The prongs (102A, 102B, 102C, 102D) end or terminate at a location distal to the end portion of the distal tip section 106 of the second tube 108. The biased bowed portions (104A, 104B, 104C, 104D) are set to a shape that bows outwardly from the second tube 108 near the distal end of the second tube 108 (once the first tube 100 is moved, as depicted in FIG. 2). Once the first tube 100 is positioned over top of the biased bowed portions (104A, 104B, 104C, 104D), the first tube 100, in use, compresses and conforms the shape of the biased bowed portions (104A, 104B, 104C, 104D) to the outer surface of the second tube 108.

Referring to the embodiment as depicted in FIG. 2, once the first tube 100 is moved to expose (at least in part) the outer surface of the second tube 108, the biased bowed portions (104A, 104B, 104C, 104D) are able to return from their stressed condition (as depicted in FIG. 1) to their relaxed position (the biased condition, as depicted in FIG. 2), and bow outwardly from the outer surface of the second tube 108 (as depicted in FIG. 2).

Referring to the embodiments as depicted in FIG. 1, FIG. 2 and FIG. 3, there may be (for instance) a quantity of at least two (2) instances of the prongs (102A, 102B, 102C, 102D) and the biased bowed portions (104A, 104B, 104C, 104D). As depicted, there are a quantity of four (4) prongs and respective bowed portions in order to facilitate biaxial tissue stretching, which may result in a greater ability to increase application of the stress forces (stretch forces) to the second biological tissue 902 (such as, the pericardial tissue). The length of the prongs (102A, 102B, 102C, 102D)

extends, preferably, past the distal end of the second tube 108. The prongs (102A, 102B, 102C, 102D) may extend, preferably, about 0.5 millimeters past the tube portal 112 of the distal tip section 106 (or of the distal end portion of the second tube 108, etc.). This arrangement may ensure that the prongs (102A, 102B, 102C, 102D) may become embedded (at least in part) to (in) the second biological tissue 902 without disturbing (or without damaging) the first biological tissue 900 (such as, the underlying myocardium), as depicted in FIG. 4 and FIG. 5.

Referring to the embodiment as depicted in FIG. 1, the biased bowed portions (104A, 104B, 104C, 104D) terminate distally at the prongs (102A, 102B, 102C, 102D). The biased bowed portions (104A, 104B, 104C, 104D) may include a stainless-steel alloy, etc., and any equivalent thereof. The dimensions of the prongs (102A, 102B, 102C, 102D) and/or the biased bowed portions (104A, 104B, 104C, 104D) may be any suitable dimension and/or configuration that is configured to engage and/or grip the tissue. It will be appreciated that the biased bowed portions (104A, 104B, 104C, 104D) are a preferred mechanism for stretching the second biological tissue 902.

Referring to the embodiment as depicted in FIG. 1, the bow angle of the biased bowed portions (104A, 104B, 104C, 104D) may be set to about 7.0 degrees, and/or about 15 millimeters (mm) from the distal end of the second tube 108 (or of the distal tip section 106). The section of the prongs (102A, 102B, 102C, 102D) may have (subtend) an angle of about 10.0 degrees in order to conform to the tapered section of the distal tip section 106 when the biased bowed portions (104A, 104B, 104C, 104D) are positioned in the contained position (as depicted in FIG. 1). These values may be changed depending on configurations and/or arrangements of the components, etc. The biased bowed portions (104A, 104B, 104C, 104D) are configured to be moved away from the outer surface of the second tube 108 (once they are released, as depicted in FIG. 2).

Referring to the embodiment as depicted in FIG. 1, the second tube 108 defines the second tube lumen 202 configured to receive (for insertion of) the ancillary device 907. The second tube 108 includes, preferably, HDPE material (high-density polyethylene) and any equivalent thereof. The second tube 108 may have a longitudinal length of about six (6.0) inches. The second tube lumen 202 (of the second tube 108) may have a diameter of about 0.035 to about 0.039 inches. The second tube 108 may have an outer diameter of about 8.0 Fr to about 8.5 Fr. The French scale or French gauge system is used to measure the size of a catheter, and is most often abbreviated as Fr. The second tube 108 includes, preferably, a reinforced stainless steel hypotube. The distal tip section 106 (the distal section of the second tube 108) is tapered to facilitate ease of insertion into, and along, the cavities and/or tissues of the patient. The second tube 108 is configured to provide an anchor for the biased bowed portions (104A, 104B, 104C, 104D) and a fixed point from which to spread tissue (therefrom). The material of the second tube 108 may be any material that provides sufficient rigidity and/or is biocompatible. The functional length of the second tube 108 may be any length, such as the length needed for percutaneous access to the heart, etc. The inner diameter of the second tube 108 may be any size, but the specified diameter is sufficient to provide compatibility for the ancillary device 907. The outer diameter of the second tube 108 may be any size. The second tube 108 may include a reinforced stainless steel hypotube that may be provided for greater device stiffness when present for traversing through patient anatomy, such as when trying to access the heart percutaneously. The distal tip section 106 does not need to be tapered for the purposes of spreading tissue (such as the pericardial tissue). The distal tip section 106 is a preferred feature that enhances usability, and the distal tip section 106 is not a necessary feature.

Referring to the embodiment as depicted in FIG. 2, the biased bowed portions (104A, 104B, 104C, 104D) are configured to be resiliently biased. The first tube 100 is moved proximally (away from the distal tip portion of the second tube 108). Movement of the first tube 100 along the retraction direction 103 exposes the biased bowed portions (104A, 104B, 104C, 104D) and, in response, the biased bowed portions (104A, 104B, 104C, 104D) resiliently move (may move to a biased condition) to a relaxed configuration (as depicted in FIG. 2), also called a bent configuration. Once the biased bowed portions (104A, 104B, 104C, 104D) resiliently move to their respective relaxed configurations, the prongs (102A, 102B, 102C, 102D) become spread away, laterally, from the distal tip (the tube portal 112) of the second tube 108. Between the end portions of the prongs (102A, 102B, 102C, 102D) and the distal tip (the tube portal 112) of the second tube 108, the radial-offset distance 101 is maintained.

Figure 15:
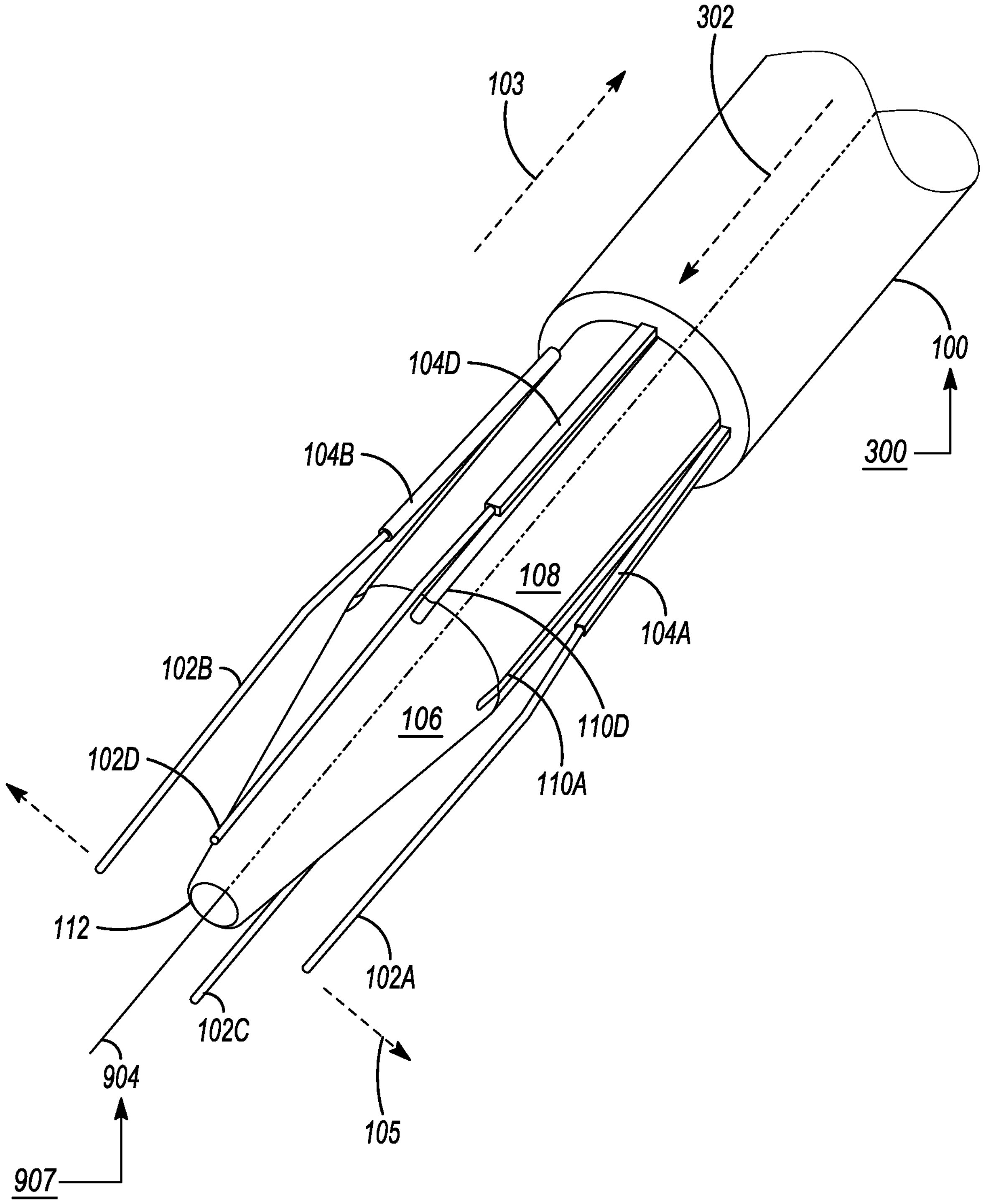
FIG. 15 depicts a side perspective view of an embodiment of the tissue-spreader assembly of FIG. 1.

Referring to the embodiment as depicted in FIG. 2, positioned on the outer surface of the second tube 108 are spaced-apart support grooves (110A, 110D), also depicted in FIG. 5 and FIG. 15. The spaced-apart support grooves (110A, 110D) respectively correspond to bowed portions (104A, 104B, 104C, 104D). The spaced-apart support grooves (110A, 110D) are configured to respectively selectively receive, and/or support, the biased bowed portions (104A, 104B, 104C, 104D); this is done, preferably, after the support bowed portions (104A, 104B, 104C, 104D are positioned in the undeployed condition, as depicted in FIG. 1.

Referring to the embodiment as depicted in FIG. 3, the cross-sectional view of the tissue-spreader assembly 300 is depicted. The cross-sectional view is taken along the cross-sectional line A-A of FIG. 2.

FIG. 4 and FIG. 5 depict side perspective views of embodiments of the tissue-spreader assembly 300 of FIG. 1.

Referring to the embodiment as depicted in FIG. 4, the tissue-spreader assembly 300 is configured to decrease the input force required to puncture the second biological tissue 902 (such as, the pericardium) relative to the first biological tissue 900 (such as, the myocardium). The tissue-spreader assembly 300 is configured to spread a section (an area, a zone) of the second biological tissue 902, while the second biological tissue 902 is positioned over (adjacent to) the first biological tissue 900. Tissue puncture may be achieved by applying stress to the second biological tissue 902 until the second biological tissue 902 fails (rips, etc.). The stress required to create a puncture through the second biological tissue 902 might be thought of as a failure threshold of the second biological tissue 902. By applying a tensile force to a region of the second biological tissue 902 using the tissue-spreader assembly 300, the stress in that localized region of the second biological tissue 902 may be increased. Thus, the additional stress input required (to be applied) to achieve tissue failure (puncture) is decreased. This is analogous to popping a balloon; the more the balloon is inflated, the greater the material of the balloon is stressed, which means it is easier to pop (puncture) the balloon (the second biological tissue 902).

Referring to the embodiment as depicted in FIG. 4, the tissue-spreader assembly 300 is configured to generate (impart) stress in (to) the second biological tissue 902 (such as the pericardium layer); this is preferably done prior to an attempt to puncture the second biological tissue 902. Once the stretching stress is applied, by the tissue-spreader assembly 300 to the second biological tissue 902, it is relatively easier to form a puncture through the second biological tissue 902 (pericardium layer) relative to the first biological tissue 900 (the myocardium layer) when a user uses the puncture device 904. The tissue-spreader assembly 300 decreases, at least in part, the chance of a user inadvertently puncturing the first biological tissue 900 (the myocardium) since it becomes easier to puncture the second biological tissue 902. For instance, the tissue-spreader assembly 300 may be utilized to facilitate the puncturing of the pericardium layer for gaining epicardial access, etc., for a heart procedure.

Referring to the embodiment as depicted in FIG. 4, a user positions the tissue-spreader assembly 300 on (proximate to) the second biological tissue 902 (the pericardium layer) with the first tube 100 in position against the second tube 108, and the prongs (102A, 102B, 102C, 102D) are positioned to engage the second biological tissue 902. The prongs (102A, 102B, 102C, 102D) may engage (embed to, or grip) the second biological tissue 902 (that is, the pericardium layer) without disturbing or gripping the first biological tissue 900 (that is, the underlying myocardium layer). The user pulls back the first tube 100 relative to the second tube 108 which exposes the biased bowed portions (104A, 104B, 104C, 104D). This releasing action causes the biased bowed portions (104A, 104B, 104C, 104D) to return to their relaxed (bowed) configuration, and to move away from the second tube 108. This action or movement causes the prongs (102A, 102B, 102C, 102D) to do the same, which causes the second biological tissue 902 (the pericardium layer) to stretch relative to the first biological tissue 900 (the underlying myocardium layer), as depicted in FIG. 5.

Referring to the embodiment as depicted in FIG. 4, the tissue-spreader assembly 300 is depicted in the undeployed condition (the contained position). The prongs (102A, 102B, 102C, 102D) are engaged with (inserted, at least in part, into) a section (an area) of the second biological tissue 902. The second biological tissue 902 includes, preferably, pericardial tissue of the heart of the patient. For instance, the pericardial tissue is a relatively thin membrane forming a sack around the heart muscle (similar to the fascia that wrap around a muscle). The second biological tissue 902 may cover the first biological tissue 900. The first biological tissue 900 includes, preferably, the myocardium (myocardium layer) of the heart of the patient. The myocardium is the contractile component of the heart. The prongs (102A, 102B, 102C, 102D) are extended and only embed themselves, at least in part, into the second biological tissue 902, and the prongs (102A, 102B, 102C, 102D) do not contact (extend into) the first biological tissue 900.

Referring to the embodiment as depicted in FIG. 4, the tissue-spreader assembly 300 in a contained position inserted into a section of the biological tissue (such as the pericardium layer). The prongs (102A, 102B, 102C, 102D) only embed themselves into the biological tissue 902 (the pericardium), but do not come into contact with the first biological tissue 900 (the underlying myocardium).

Referring to the embodiment as depicted in FIG. 5, the tissue-spreader assembly 300 is placed in the deployed condition (the spread position). The prongs (102A, 102B, 102C, 102D) have moved laterally and have stretched the second biological tissue 902 (the pericardial tissue) such that they are embedded into but not embedded (or engaged with) the first biological tissue 900 (that is, the underlying myocardium). The prongs (102A, 102B, 102C, 102D) are configured to increase the stress in the stretched section of the second biological tissue 902 (the pericardial tissue) which lowers the required force to puncture the second biological tissue 902.

Referring to the embodiments as depicted in FIG. 4 and FIG. 5, the tissue-spreader assembly 300 is configured to be selectively inserted into the patient 903 having the first biological tissue 900 and the second biological tissue 902 positioned proximate to the first biological tissue 900. The tissue-spreader assembly 300 is also configured to be maneuvered (and positioned) proximate to the second biological tissue 902. The tissue-spreader assembly 300 is also configured to selectively engage (contact), at least in part, an area of the second biological tissue 902 (but) without engaging (contacting) the first biological tissue 900 after the tissue-spreader assembly 300, in use, is maneuvered (and positioned) proximate to the second biological tissue 902. The tissue-spreader assembly 300 is also configured to selectively spread, at least in part, the area of the second biological tissue 902, and maintain the area of the second biological tissue 902 in a spread-apart condition; this is done, preferably, after the tissue-spreader assembly 300, in use, selectively engages (contacts), at least in part, the area of the second biological tissue 902 (but) without engaging (contacting) the first biological tissue 900. The definition of selectively spread includes stretching the second biological tissue 902 in any manner, such as a uniaxial manner, a biaxial manner and/or an omni-axial manner, to increase the stress so that the second biological tissue 902 may easily separate from the first biological tissue 900. The definition of selectively engage includes any manner of gripping, selecting, embedding an area, or a region, of the second biological tissue 902 separately from the first biological tissue 900.

Referring to the embodiments as depicted in FIG. 4 and FIG. 5, the second biological tissue 902 is positioned to be in contact with the first biological tissue 900.

Referring to the embodiments as depicted in FIG. 4 and FIG. 5, the second biological tissue 902 is positioned over the first biological tissue 900.

Referring to the embodiments as depicted in FIG. 4 and FIG. 5, the tissue-spreader assembly 300 is also configured to selectively disengage from the area of the second biological tissue 902.

Referring to the embodiments as depicted in FIG. 4 and FIG. 5, the tissue-spreader assembly 300 is also configured to selectively permit the area of the second biological tissue 902 to become relaxed from the spread-apart condition.

Referring to the embodiments as depicted in FIG. 4 and FIG. 5, the tissue-spreader assembly 300 is also configured to selectively disengage from the area of the second biological tissue 902.

Referring to the embodiments as depicted in FIG. 4 and FIG. 5, the tissue-spreader assembly 300 includes prongs (102A, 102B, 102C, 102D) configured to selectively engage (contact), at least in part, the area of the second biological tissue 902. The prongs (102A, 102B, 102C, 102D) are also configured to selectively spread, at least in part, the area of the second biological tissue 902 after the prongs (102A, 102B, 102C, 102D) selectively engage (contact), at least in part, the area of a second biological tissue 902.

Referring to the embodiments as depicted in FIG. 4 and FIG. 5, the tissue-spreader assembly 300 is also configured to provide a guide path 302 configured to guide, at least in part, an ancillary device 907 toward the area of the second biological tissue 902 while the area of the second biological tissue 902 remains spread apart by the tissue-spreader assembly 300 and while the first biological tissue 900 remains unengaged with the tissue-spreader assembly 300.

Referring to the embodiments as depicted in FIG. 4 and FIG. 5, the tissue-spreader assembly 300 is also configured to selectively disengage from the area of the second biological tissue 902 after the ancillary device 907 has completed application of treatment to the area of the second biological tissue 902.

Referring to the embodiments as depicted in FIG. 4 and FIG. 5, the ancillary device 907 is configured to treat the area of the second biological tissue 902 while the area of the second biological tissue 902 remains spread apart by the tissue-spreader assembly 300.

Referring to the embodiments as depicted in FIG. 4 and FIG. 5, the ancillary device 907 is configured to contact, at least in part, the area of the second biological tissue 902 (but) without contacting the first biological tissue 900 after the area of the second biological tissue 902 is spread apart by the tissue-spreader assembly 300.

Referring to the embodiments as depicted in FIG. 4 and FIG. 5, the ancillary device 907 includes a puncture device 904 configured to impart a puncture force sufficient for puncturing the second biological tissue 902 (but) without puncturing the first biological tissue 900 after the area of the second biological tissue 902 is selectively spread apart by the tissue-spreader assembly 300.

Referring to the embodiments as depicted in FIG. 4 and FIG. 5, there is depicted a method of selectively spreading the second biological tissue 902 positioned proximate to the first biological tissue 900 of the patient 903. The method includes selectively inserting a tissue-spreader assembly 300 into the patient 903. The method also includes maneuvering (and positioning) the tissue-spreader assembly 300 to a position located proximate to the second biological tissue 902. The method also includes using the tissue-spreader assembly 300 to selectively engage (contact), at least in part, an area of the second biological tissue 902 (but) without engaging (contacting) the first biological tissue 900 after the tissue-spreader assembly 300, in use, is maneuvered (and positioned) proximate to the second biological tissue 902. The method also includes using the tissue-spreader assembly 300 to selectively spread, at least in part, the area of the second biological tissue 902, and maintain the area of the second biological tissue 902 in a spread-apart condition after the tissue-spreader assembly 300, in use, selectively engages (contacts), at least in part, the area of the second biological tissue 902 (but) without engaging (contacting) the first biological tissue 900. The method may be utilized when the second biological tissue 902 is positioned to be in contact with the first biological tissue 900. The method may be utilized when the second biological tissue 902 is positioned over the first biological tissue 900.

FIG. 6 to FIG. 13 depict side schematic views of embodiments of the tissue-spreader assembly 300 of FIG. 1.

Referring to the embodiments of FIG. 6 to FIG. 13, the prongs (102A, 102D) and the ancillary device 907 (or the distal puncture tip 906 of the puncture device 904) are utilized to puncture the second biological tissue 902 (such as the pericardium layer of the heart, etc., to facilitate epicardial access). The user positions the distal end of the tissue-spreader assembly 300 proximate to the second biological tissue 902. The prongs (102A, 102D) are utilized to become embedded, or to grip, the second biological tissue 902. The prongs (102A, 102D) are moved from the undeployed condition (as shown in FIG. 1) to the deployed condition (as shown in FIG. 2). For instance, the user may shift the first tube 100 proximally on the tissue-spreader assembly 300 causing the biased bowed portions (104A, 104B, 104C, 104D) along the second tube 108 to become exposed, etc. The biased bowed portions (104A, 104D) return to their relaxed configuration (as depicted in FIG. 2, angled outwards from the second tube 108) and cause the prongs (102A, 102D) to move laterally relative to the distal tip of the tissue-spreader assembly 300 (or of the second tube 108), stretching the second biological tissue 902 relative to the first biological tissue 900 (such as the myocardial tissue, etc.). The ancillary device 907 (or the distal puncture tip 906 of the puncture device 904) is delivered, via the tissue-spreader assembly 300 (such as through the second tube lumen 202 of the second tube 108), and is used to puncture the second biological tissue 902. The puncture force required may be relatively lower than what may be required without utilization of the tissue-spreader assembly 300 given the increased stress imposed to (on) the second biological tissue 902 as a result of the stretching applied by the tissue-spreader assembly 300, such as by the prongs (102A, 102D), etc.

Figure 6:
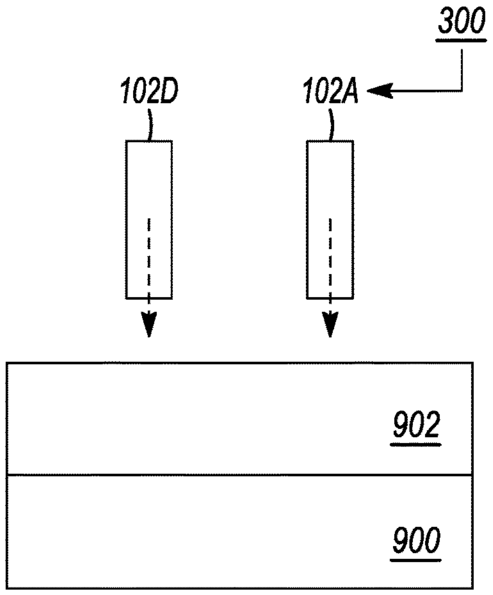
FIG. 6 to FIG. 13 depict side schematic views of embodiments of the tissue-spreader assembly of FIG. 1.

Referring to the embodiment as depicted in FIG. 6, the prongs (102A, 102D) of the tissue-spreader assembly 300 are moved toward the second biological tissue 902 (from the undeployed condition as depicted in FIG. 1 to the deployed condition). It will be appreciated that FIG. 7 to FIG. 12 depict the tissue-spreader assembly 300 in the various states of the deployed condition. The first biological tissue 900 is positioned to be in contact with (positioned proximate to) the second biological tissue 902.

Figure 7:
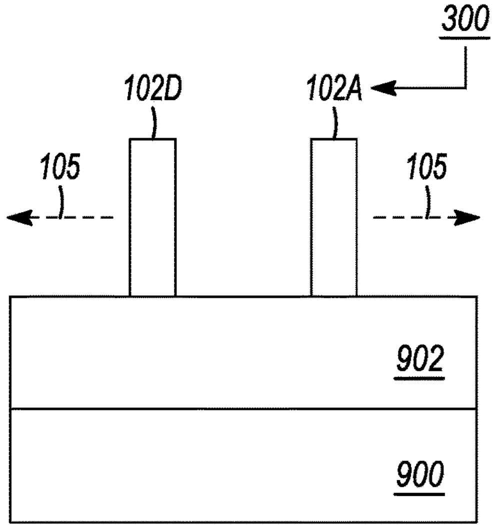

Referring to the embodiment as depicted in FIG. 7, the prongs (102A, 102D) of the tissue-spreader assembly 300 engage (securely engage, contact) the second biological tissue 902. The prongs (102A, 102D) are spread apart while the prongs (102A, 102D) remain engaged (securely engaged) with the second biological tissue 902. The first biological tissue 900 is, preferably, undamaged by the movements of the prongs (102A, 102D).

Figure 8:
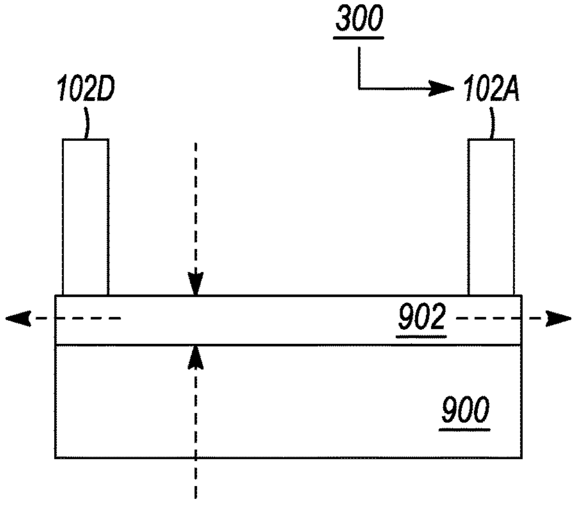

Referring to the embodiment as depicted in FIG. 8, the prongs (102A, 102D) of the tissue-spreader assembly 300 are maintained in a wider spaced apart condition while the prongs (102A, 102D) continue to engage the second biological tissue 902. The second biological tissue 902 becomes thinner (stretched out) while the prongs (102A, 102D) continue to engage the second biological tissue 902. The prongs (102A, 102D) impart, to the second biological tissue 902, stretching forces while the prongs (102A, 102D) continue to engage the second biological tissue 902. The first biological tissue 900 remains, preferably, unstressed by the movements of the prongs (102A, 102D).

Figure 9:
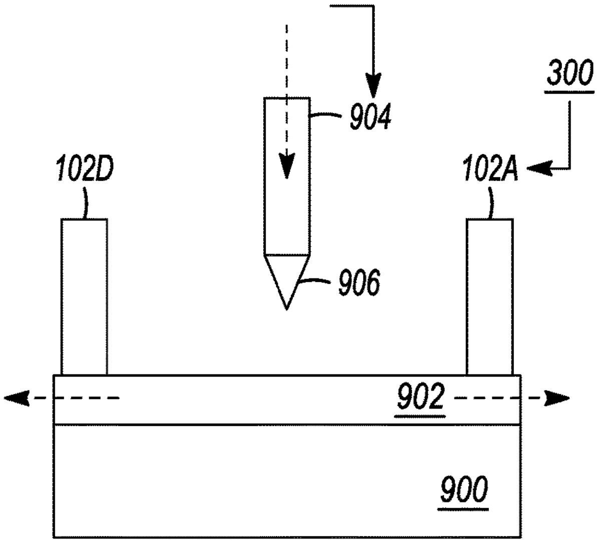

Referring to the embodiment as depicted in FIG. 9, the ancillary device 907 (or the distal puncture tip 906 of the puncture device 904) is moved toward the second biological tissue 902, while the second biological tissue 902 is maintained in a spread condition by the prongs (102A, 102D) of the tissue-spreader assembly 300. The prongs (102A, 102D) of the tissue-spreader assembly 300 impart, and maintain, stretching forces to the second biological tissue 902, while the ancillary device 907 (or the distal puncture tip 906 of the puncture device 904) is moved toward the second biological tissue 902 so that the ancillary device 907 may puncture the second biological tissue 902 without puncturing (damaging) the first biological tissue 900.

Figure 10:
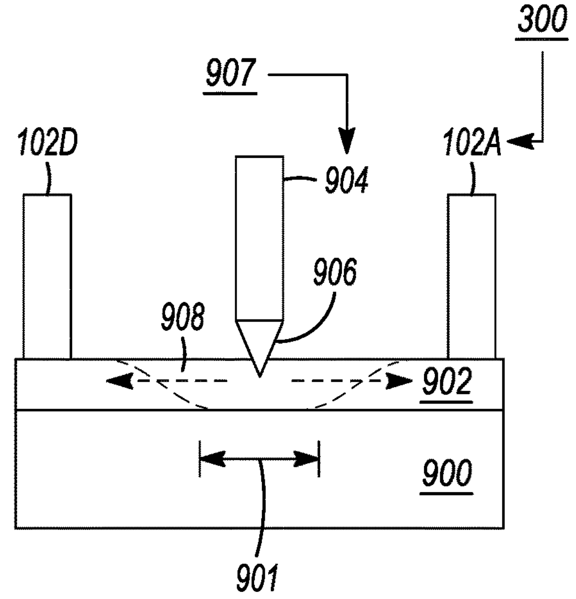

Referring to the embodiment as depicted in FIG. 10, the ancillary device 907 (or the distal puncture tip 906 of the puncture device 904) is moved just enough so that the ancillary device 907 manages to simply pierce (puncture)

the second biological tissue 902. The second biological tissue 902 is maintained in a stretched condition by the prongs (102A, 102D) of the tissue-spreader assembly 300. The stretch forces, which are set-up in the second biological tissue 902 by the prongs (102A, 102D), become free to form (create) the exposed passageway 908 extending through the second biological tissue 902, thereby revealing the exposed surface 901 of the first biological tissue 900. The second biological tissue 902 is, preferably, damaged by the movements (operations) of the ancillary device 907 (or the distal puncture tip 906 of the puncture device 904). The first biological tissue 900 is, preferably, undamaged by the movements (operations) of the ancillary device 907 (or the distal puncture tip 906 of the puncture device 904).

Figure 11:
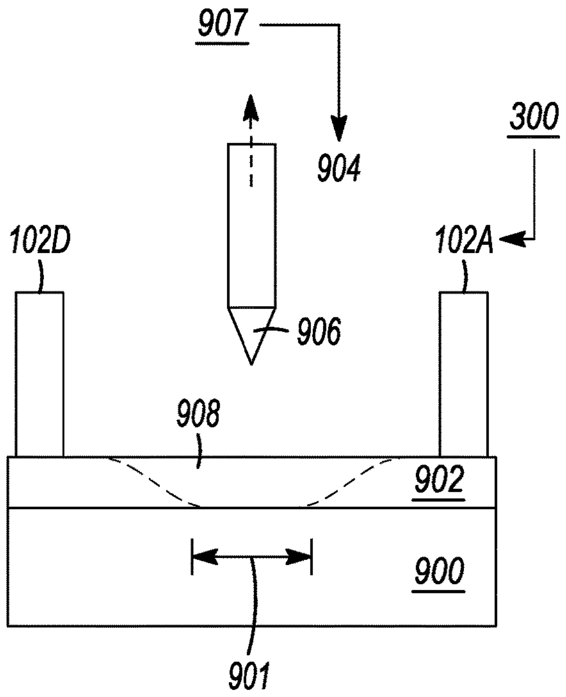

Referring to the embodiment as depicted in FIG. 11, the ancillary device 907 (or the distal puncture tip 906 of the puncture device 904) is retracted away from the second biological tissue 902, while the prongs (102A, 102D) of the tissue-spreader assembly 300 are maintained in engaged contact with the second biological tissue 902. The first biological tissue 900 is, preferably, undamaged by the movements of the ancillary device 907 (or the distal puncture tip 906 of the puncture device 904). The ancillary device 907 (or the distal puncture tip 906 of the puncture device 904) has pierced (punctured) the second biological tissue 902, and the stresses set up in the second biological tissue 902 have formed the exposed passageway 908 extending through the second biological tissue 902, thereby revealing the exposed surface 901 of the first biological tissue 900.

Figure 12:
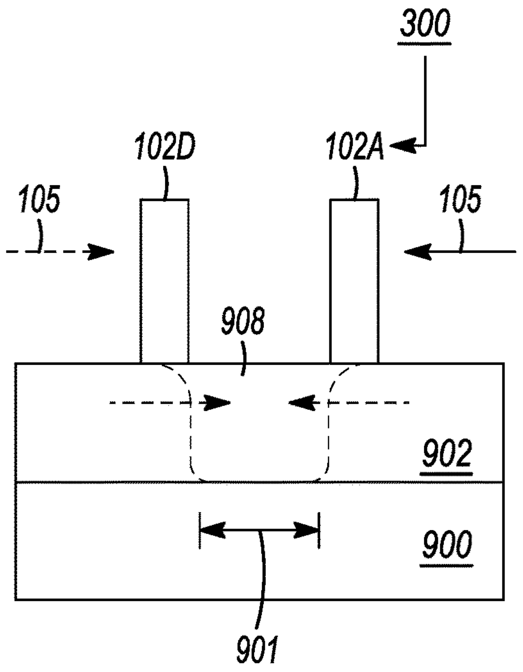

Referring to the embodiment as depicted in FIG. 12, the prongs (102A, 102D) of the tissue-spreader assembly 300 are moved (translated) toward each other along the prong-movement direction 105. The second biological tissue 902 regains its normal (unstressed) condition or thickness after the prongs (102A, 102D) are moved (translated) toward each other. The first biological tissue 900 remains, preferably, undamaged by the movements of the prongs (102A, 102D). The second biological tissue 902 defines the exposed passageway 908 (a tear, etc.) that extends through the second biological tissue 902, thereby revealing the exposed surface 901 of the first biological tissue 900. The size of the exposed passageway 908 may become relatively smaller (compared to the size depicted in FIG. 11) after the prongs (102A, 102D) are moved (translated) toward each other.

Figure 13:
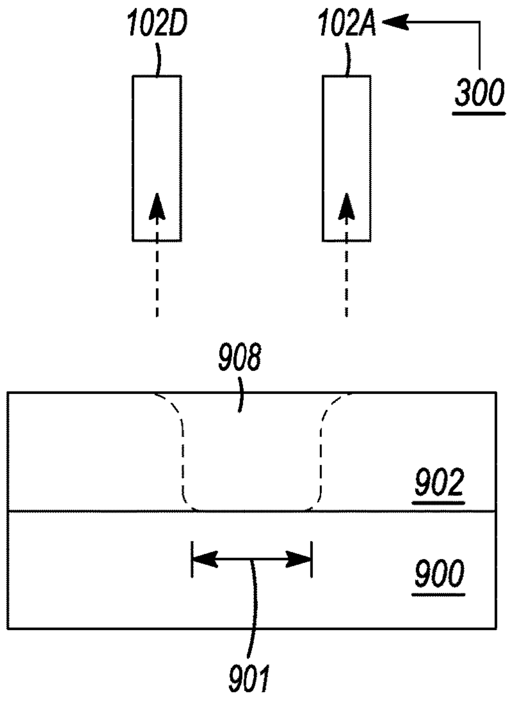

Referring to the embodiment as depicted in FIG. 13, the prongs (102A, 102D) of the tissue-spreader assembly 300 are moved (translated) away from the second biological tissue 902 (from the deployed condition as depicted in FIG. 2 toward the undeployed condition as depicted in FIG. 1). The second biological tissue 902 regains a relaxed condition, unstressed by the prongs (102A, 102D). The second biological tissue 902 has returned to (or regained) its normal thickness, similar to the thickness prior to usage (application) of the prongs (102A, 102D). The first biological tissue 900 is, preferably, not damaged by the movements of the prongs (102A, 102D) and/or the ancillary device 907 (or the puncture device 904, etc.). The second biological tissue 902 defines the exposed passageway 908 formed by the usage of the prongs (102A, 102D) and/or the ancillary device 907 (or the puncture device 904, etc.). The exposed passageway 908 extends through the thickness of the second biological tissue 902. The exposed surface 901 of the first biological tissue 900 is now ready to be accessed by a treatment device and/or a procedure (not depicted and not described).

Figure 14:
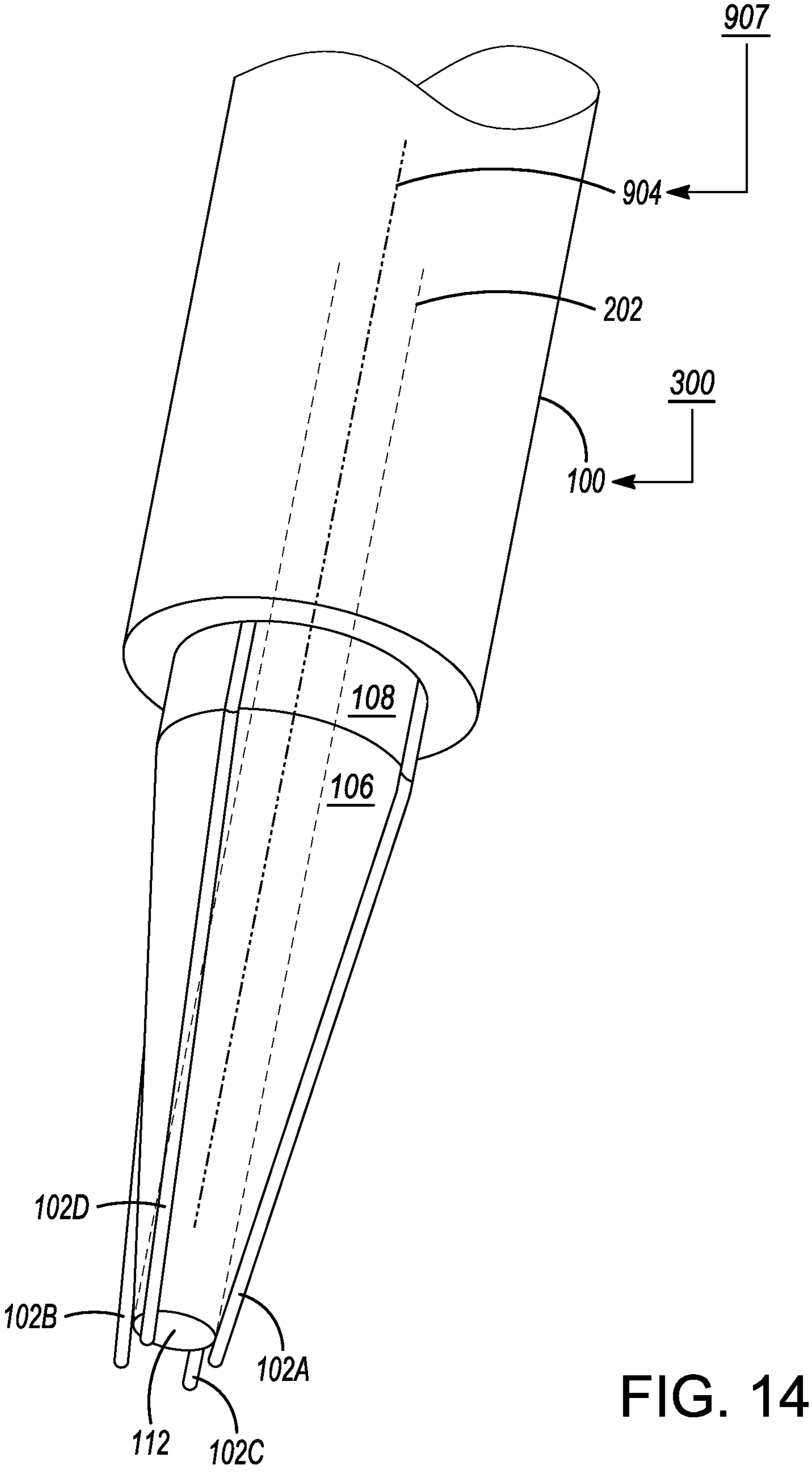
FIG. 14 depicts a side perspective view of an embodiment of the tissue-spreader assembly of FIG. 1.

FIG. 14 depicts a side perspective view of an embodiment of the tissue-spreader assembly 300 of FIG. 1.

Referring to the embodiment as depicted in FIG. 14, the tissue-spreader assembly 300 is placed in the undeployed condition (the contained position). The second tube lumen 202 of the second tube 108 is configured to receive the ancillary device 907, etc. The second tube 108 defines the tube portal 112, from which the ancillary device 907 may be selectively extended therefrom, etc.

FIG. 15 depicts a side perspective view of an embodiment of the tissue-spreader assembly 300 of FIG. 1.

Referring to the embodiment as depicted in FIG. 15, the tissue-spreader assembly 300 is depicted in the deployed condition (the spread configuration).

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open-ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for non-limiting embodiments (examples). It is understood that the non-limiting embodiments are merely illustrative as examples.

The invention claimed is:

1. An apparatus, comprising:
a tissue-spreader assembly configured to be selectively inserted into a patient having a first biological tissue and a second biological tissue being positioned over the first biological tissue, and to be maneuvered proximate to the second biological tissue; and
the tissue-spreader assembly further configured to selectively engage an area of the second biological tissue without engaging the first biological tissue after the tissue-spreader assembly, in use, is maneuvered proximate to the second biological tissue; and
the tissue-spreader assembly also configured to provide a guide path for an ancillary device;
wherein the tissue-spreader assembly includes:
a first tube;
a second tube configured to be received within the first tube, wherein the second tube includes the guide path; and
prongs configured to selectively engage or spread the area of the second biological tissue, the prongs surrounding a circumferential surface of the second tube.

2. The apparatus of claim 1, wherein:
the first tube and the second tube are coaxially aligned with each other after the second tube is received within, and along, the longitudinal length of the first tube.

3. The apparatus of claim 1, wherein:
the tissue-spreader assembly includes:
prongs movable between an undeployed condition and a deployed condition; and
the prongs being configured to engage the area of the second biological tissue.

4. The apparatus of claim 3, wherein:
the prongs include:
hollow tubes with open portals being configured to face the second biological tissue; and
said open portals being configured to be embedded into the second biological tissue.

5. The apparatus of claim 3, wherein:
the first tube and the second tube being coaxially aligned with each other after the second tube is received within the first tube; and
the prongs extend past a distal end of the second tube after the prongs are moved from the undeployed condition to the deployed condition.

6. The apparatus of claim 3, wherein:
the first tube and the second tube being coaxially aligned with each other after the second tube is received within the first tube; and
the first tube is configured to maneuver the prongs from the undeployed condition to the deployed condition, after the first tube is retracted proximally over the second tube.

7. The apparatus of claim 3, wherein:
the tissue-spreader assembly includes:
the first tube and the second tube being coaxially aligned with each other after the second tube is received within the first tube; and
biased bowed portions, the prongs extending from the biased bowed portions; and
the biased bowed portions being configured to be positioned between the first tube and the second tube after the tissue-spreader assembly is placed in the undeployed condition; and
the biased bowed portions also being configured to be compressed after the tissue-spreader assembly is placed in the undeployed condition.

8. The apparatus of claim 7, wherein:
positioned on an outer surface of the second tube are support grooves; and
the support grooves respectively correspond to bowed portions; and
the support grooves are configured to receive and support the biased bowed portions after the support bowed portions are positioned in the undeployed condition.

9. The apparatus of claim 8, wherein:
the prongs extend from the biased bowed portions; and
the prongs terminate at a location distal to an end portion of the second tube.

10. The apparatus of claim 7, wherein:
the first tube is configured to force compression of the biased bowed portions against the second tube once the first tube is moved to cover the biased bowed portions.

11. The apparatus of claim 7, wherein:
the first tube is configured to reduce a bow angle formed by the biased bowed portions.

12. The apparatus of claim 7, wherein:
the biased bowed portions are set to a shape that bows outwards from the second tube near a distal end of the second tube once the first tube is moved along the patient; and
the first tube is configured to compress and conform the biased bowed portions to an outer surface of the second tube after the first tube is positioned over top of the biased bowed portions.

13. The apparatus of claim 7, wherein:
the biased bowed portions are configured to return from a stressed condition to a relaxed condition after the first tube is moved to expose an outer surface of the second tube.

14. The apparatus of claim 1, wherein:
the guide path is configured to guide an ancillary device toward the area of the second biological tissue while the area of the second biological tissue remains spread apart by the tissue-spreader assembly and while the first biological tissue remains unengaged with the tissue-spreader assembly.

15. The apparatus of claim 14, wherein:
the tissue-spreader assembly also configured to selectively disengage from the area of the second biological tissue after the ancillary device has completed application of treatment to the area of the second biological tissue.

16. The apparatus of claim 14, wherein:
the ancillary device being configured to treat the area of the second biological tissue while the area of the second biological tissue remains spread apart by the tissue-spreader assembly.

17. The apparatus of claim 14, wherein:
the ancillary device is configured to contact the area of the second biological tissue without contacting the first biological tissue after the area of the second biological tissue is spread apart by the tissue-spreader assembly; and
the ancillary device includes a puncture device configured to impart a puncture force sufficient for puncturing the second biological tissue without puncturing the first biological tissue after the area of the second biological tissue is selectively spread apart by the tissue-spreader assembly.

18. An apparatus, comprising:
a tissue-spreader assembly configured to be selectively inserted into a patient having a first biological tissue and a second biological tissue being positioned proximate to the first biological tissue, and to be maneuvered proximate to the second biological tissue; and
the tissue-spreader assembly further configured to selectively engage an area of the second biological tissue without engaging the first biological tissue after the tissue-spreader assembly, in use, is maneuvered proximate to the second biological tissue; wherein:
the tissue-spreader assembly includes:
hollow tubes being movable between an undeployed condition and a deployed condition; and
the hollow tubes including open portals being configured to engage the area of the second biological tissue.

19. An apparatus, comprising:
a tissue-spreader assembly configured to be selectively inserted into a patient having a first biological tissue and a second biological tissue being positioned proximate to the first biological tissue, and to be maneuvered proximate to the second biological tissue; and
the tissue-spreader assembly further configured to selectively engage an area of the second biological tissue without engaging the first biological tissue after the tissue-spreader assembly, in use, is maneuvered proximate to the second biological tissue; wherein:
the tissue-spreader assembly includes:
a first tube and a second tube; wherein:
positioned on an outer surface of the second tube are spaced-apart support grooves configured to receive and support biased bowed portions.

* * * * *